United States Patent [19]

Nyiri et al.

[11] 4,064,015
[45] Dec. 20, 1977

[54] CONTROL OF BIOSYNTHESIS IN SUBMERGED CULTURE

[75] Inventors: Laszlo K. Nyiri; Gizella M. Tóth, both of Bethlehem; Douglass V. Parmenter, Allentown; Calidas S. Krishnaswami, Whitehall, all of Pa.

[73] Assignee: New Brunswick Scientific Co., Inc., Edison, N.J.

[21] Appl. No.: 576,902

[22] Filed: May 12, 1975

[51] Int. Cl.$^2$ ............................................. C12B 1/00
[52] U.S. Cl. .................................. 195/108; 195/109; 195/115; 195/117
[58] Field of Search ............... 195/115, 104, 108, 109, 195/117, 118, 82, 49, 103.5 R

[56] References Cited

U.S. PATENT DOCUMENTS

| | | | |
|---|---|---|---|
| 2,822,319 | 2/1958 | Monod | 195/115 |
| 3,002,894 | 10/1961 | Rungaldier et al. | 195/117 |
| 3,926,737 | 12/1975 | Wilson et al. | 195/117 |

Primary Examiner—R. B. Penland
Attorney, Agent, or Firm—Blum, Moscovitz, Friedman & Kaplan

[57] ABSTRACT

Continuous control of biosynthesis process conditions on the basis of measurable quantities in the off-gases from the process and calculated quantities derived from said measured quantities provides for optimization of reaction conditions with respect to maximum output rate of selected product. Where the selected product is a mix of cell mass and ethyl alcohol ranging from virtually all cell mass with negligible alcohol to the maximum alcohol content which the cell can tolerate, optimization depends on maintaining the ratio of carbon to nitrogen in the nutrient feed at a level appropriate to the desired product mix. The calculated quantities, including the time derivative of the rate of oxygen uptake, are used for essentially continuous control of the rates of feed of individual nutrients and other selected essential variables as a means of optimizing the process.

19 Claims, 3 Drawing Figures

CONTROL OF BIOSYNTHESIS IN SUBMERGED CULTURE

BACKGROUND OF THE INVENTION

Fermentation process, ranging from the production of alcoholic beverages to the production of antibiotics have a long history during wich a mass of experimental studies and publications including both the results of such studies and theories as to the mechanisms involved have been produced. Theories, of course, are based on observation, and then are used as the basis for improving process conditions, the objective being to optimize the process so as to increase both the quality and the quantity of product. Further, it is an object to cut the costs of production, particularly so far as raw materials and the yield therefrom are concerned.

In general, control of process variables has been based on correlations established between selected values of process variables and the quantity and quality of product output. However, measurement of quantity and quality of output during the course of a process is a relatively slow procedure, so that using such a method, there is, of necessity, a substantial lag between sampling of the output and the effecting of a change in process variables to correct any deviation from optimum output. Moreover, the nature of the output will change during the course of a biosynthesis process so that the levels at which the process variables should be held will similarly change during the course of a process, such a situation being characteristic, particularly, of batch processes.

As a result of the time lag, as will be shown, biosynthesis processes have frequently been run under conditions which deviate substantially from optimum. Also, so-called "laws" have been formulated and "effects" have been discovered which have been proved to be erroneous. An excellent example of the latter is the so-called "Pasteur effect" which is concerned with the suppression of formation of alcohol during the growth of yeast in the presence of oxygen. It has been thought that production of ethyl alcohol, when yeast is the desired end product, will be suppressed if the oxygen feed rate is high and the concentration of fermentable carbohydrate in the culture is maintained at a low level. In fact, the so-called "Zulauf" process on which a number of patents has issued requires maintaining the carbohydrate level below 0.0004%. To keep the carbohydrate level this low, the molasses used as the nutrient must be added very slowly. Since the concentration of molasses is low, the process itself is necessarily slow. As a result, the rate of production of yeast is likewise slow. Accordingly, production rates of yeast or cell mass are in the range of 1.2 g/l hour. As will be shown, it is possible to suppress the formation of alcohol and yet achieve a much higher rate of production of cell mass by other means.

In view of the large number of variables involved in the usual biosynthesis process, the availability of small and relatively inexpensive calculators or microprocessors has generated great interest in applying such devices to the control of such processes. However, the combining of the microprocessor with appropriate sensors for determining the reaction conditions and then controlling process variables has not always been fully successful. A major reason, as is implied above, is that correlations between operating variables and product output have been sought as the basis for controlling the process. And, as aforenoted, substantial lags interfere with on-line, real time control. It will be shown intermediate quantities, i.e. quantities which can be calculated from measurements provided by sensors, and which can be correlated both with product output and with operating conditions provide a superior method of controlling biosynthesis processes.

SUMMARY OF THE INVENTION

In an aerobic biosynthesis, oxygen is consumed and carbon dioxide is evolved. The rate of oxygen supply is a controllable variable which experiment has shown to be a significant factor with respect to efficacy of the process. Other controllable variables which affect process efficacy are process temperature, process pressure, pH, and dissolved $O_2$ as well as the rate of feed of individual nutrients. Although not controllable, yet an essential variable is the elapsed time since the inception of the process since the metabolic activity of the cells changes with time. Of course, it is recognized that where the process is run on an essentially continuous basis, the culture reaches an essentially constant composition, i.e. steady state.

Where the biosynthesis process consists of growth of yeast cells, both cell mass, frequently referred to as "single cell protein", and ethyl alcohol are produced. Applicants have shown that the process can be optimized with respect to product output by determining the effect of making arbitrary changes in the aforenoted essential, controllable variables and establishing the effect of such changes on RQ defined as $dCO_2/dO_2$, RQ being calculated from determinations of the $CO_2$ evolution rate and the $O_2$ uptake or consumption rate by the culture. The second step in establishing the control relationships is to correlate product output rate and composition, i.e., quality, with RQ. Once this is done, the process can be controlled by adjustment of the essential, controllable variables to maintain RQ at the desired value corresponding to the correlation established between RQ and the product output. It is recognized, of course that the value for RQ will vary with elapsed time since the beginning of the process when the process is run on a batch basis despite control action to bring RQ to a predetermined value.

Determination of the gas flow rate, temperature and presure and $O_2$ consumption rate and the $CO_2$ evolution rate are carried out essentially continuously. Consequently calculation of RQ is carried out essentially continuously. The calculation is effected by means of a conventional electronic calculator interfaced with the instruments measuring the $O_2$ consumption and $CO_2$ release rates. Deviations of RQ are used to generate signals to controllers which make appropriate changes in the essential, controlled variables to return RQ to the desired value.

During the production of cell mass where it is desired that the production of alcohol be suppressed and the production of cell mass be maximized, the fermentation being carried out on a continuous basis it is known that RQ should be maintained at an RQ value of about 1.0. To maintain RQ at this value, we have found that the feed ratio of carbon to nitrogen must be maintained at between about 2 and 7. More specifically, the electronic calculator-based controller should hold the carbon-to-nitrogen feed ratio near 2 during batch operation and near 5 during continuous or semicontinuous operation.

The carbon to nitrogen feed ratio is herein termed C/N and defined as the weight of carbon supplied as fermentable carbohydrate divided by the weight of nitrogen supplied in biologically available form. This form may be ammonia, ammonium hydroxide, ammonium phosphate, ammonium sulphate and mixtures thereof or as nitrogen in the form of an organic compound. The nitrogen-containing nutrients are fed in a ratio such that sulphate and phosphate ion concentrations do not rise above the levels at which inhibition of the metabolic activity occurs.

When the production of alcohol is to be maximized, RQ is preferably held between 3 and 7. The concentration of ethyl alcohol in the culture is optimum of about 5%, and cannot rise above 8% at which level the alcohol content generally becomes toxic. At a level of about 5% the rate of production is maximized. Using a conventional technique it was established that a suitable C/N range for ethyl alcohol production is 15 –22; about 17.5 to 18.5 is optimum.

Using a microprocessor for accepting data from sensors, carrying out the necessary calculations and controlling the essential, controllable variables on a real-time, on-line basis in response to said calculations, conversions of carbon to selected product at yields as high as 65% can be obtained, whereas in prior art, the maximum yield was about 50%.

A further degree of control is achieved by calculating $d^2O_2/dt^2$ the first derivative of the rate of oxygen uptake by the culture, and increasing the rate of nutrient supply, and in particular, metabolizable C, when $d^2O_2/dt^2$ is positive and decreasing said rate when this quantity is negative. By this means production of cell mass at rates as high as 7.5 g/l hour are achieved, prior art processes yielding cell mass at a rate of only about 1.2 g/l hour. The output rate per unit of fermentor or biosynthesis tank volume is thus increased by a factor of about 6.

Accordingly, an object of the present invention is a method of carrying out a biosynthesis process under automatic control so as to increase the product output rate and to control the product mix.

Another object of the present invention is a method of controlling a biosynthesis process by essentially continuous determination of components in effluent gases, on-line, real-time calculation of at least one quantity which has been correlated with the rate of output of product, and control of essential, controllable variables to bring said calculated quantity to a desired value and then maintain said calculated quantity at that value.

A further object of the present invention is a method of controlling a metabolic process wherein cell mass or cell mass in combination with ethyl alcohol constitutes a desired product on the basis of determining $CO_2$ evolution and $O_2$ consumption and calculating feed rates of nutrients and air supply rate to maintain said RQ at a desired level which has been previously established as corresponding to optimization of product output.

An important object of the present invention is control of a fermentation process so that cell mass constitutes virtually the entire product or cell mass in combination with a desired quantity of ethyl alcohol is obtained, the desired product mix being obtained by control of the ratio of carbon to biologically available nitrogen in the nutrients supplied to the fermentor.

A significant object of the present invention is a method of controlling a metabolic process so as to maximize the rate of output of selected product through control of the ratio of carbon to nitrogen in the nutrient feed and control of the rate of feed of nutrient on the basis of the physiological condition of the culture as expressed by $CO_2$ release, and $O_2$ consumption rates as well as their ratio, RQ.

Another important object of the present invention is an apparatus for carrying out and controlling a metabolic process so as to maximize the rate of output of selected product through control of the ratio of carbon to nitrogen in the nutrient feed and control of the rate of feed of nutrient.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
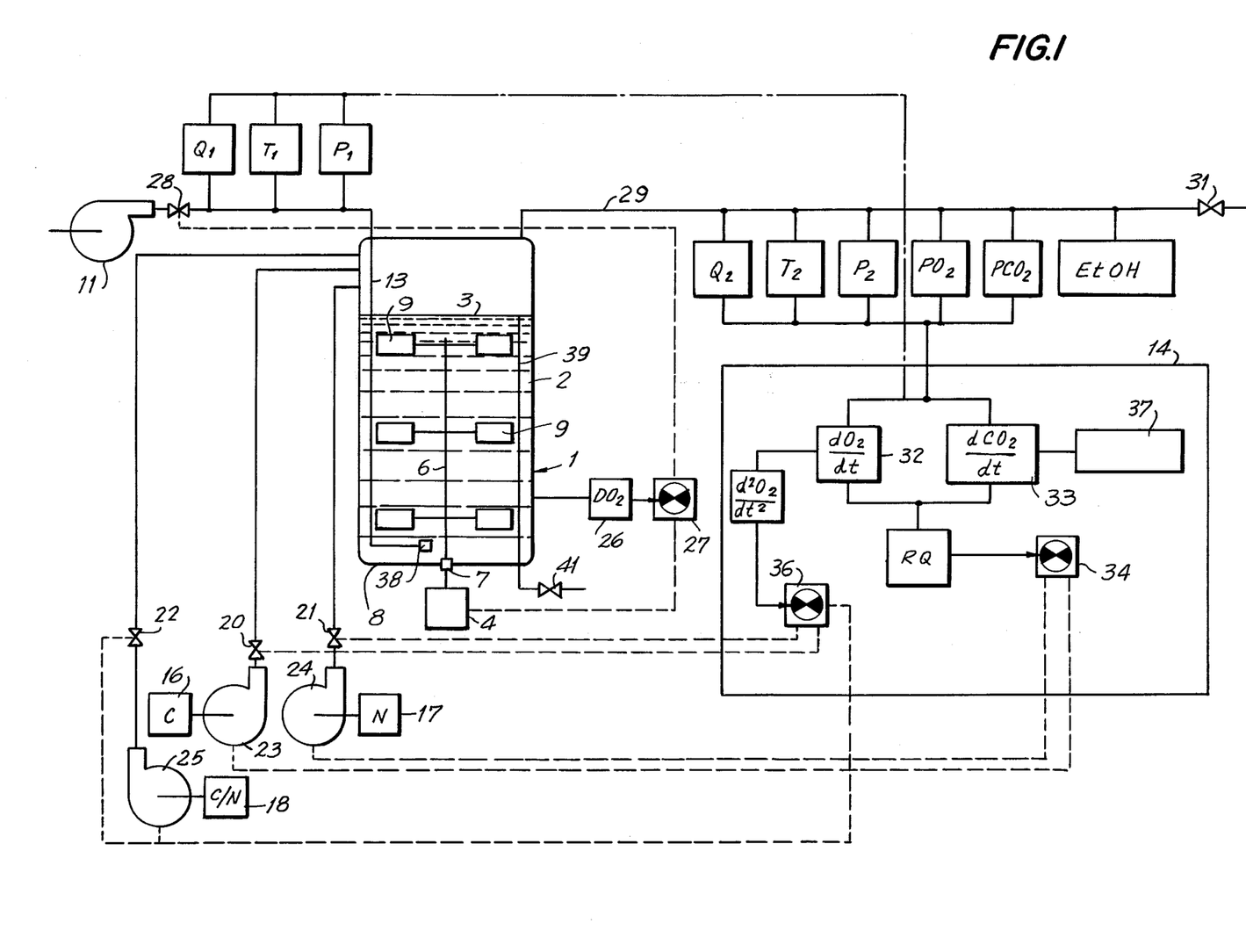
FIG. 1 shows schematically apparatus for carrying out the process of the present invention.

Biosynthesis of cell mass and ethyl alcohol in accordance with the present invention is carried out in apparatus as shown schematically in FIG. 1. FIG. 1 shows apparatus suitable for fermentation, fermentation being considered representative of biosynthesis cell mass including primary (protein) and secondary metabolites (EtOH).

In accordance with FIG. 1, fermentation takes place in a tank represented generally by the reference numeral 1. Tank 1 has therein culture medium 2, the liquid level of culture medium 2 being indicated by the reference numeral 3. Since fermentation reactions, in general, are exothermic, the tank temperature must be controlled as by fitting with a cooling jacket (not shown) through which cooling water can be run. The temperature is held at 30° C, known to be optimum for the process depicted. Agitation of the liquid contents is by variable speed motor 4 having a shaft 6 passing through a liquid-tight seal 7 in bottom 8 of tank 1. Shaft 6 is fitted with paddles 9 to provide vigorous stirring of culture medium 2. Pump 11 forces sterile air through control valve 12 and line 13 into the culture medium.

Sensors $Q_1$, $T_1$ and $P_1$ respectively measure input airflow rate, air temperature and air pressure and transmit the information thus gathered to an electronic calculator 14. As will become evident this information is primarily confirmatory and is not completely necessary for satisfactory operation of the system. For this reason, line 42 electronic calculator 14 is shown in dot-dash form. Nutrient feed tanks, 16, 17 and 18 are respectively labelled C, N and C/N for reasons which will become evident. Valves 20, 21 and 22 are remotely controllable and make it possible to adjust the rate at which feed is supplied from each of the tanks 16, 17 and 18. Transfer of nutrient is carried out by use of pumps 23, 24 and 25 from tanks 16, 17 and 18 repsectively.

As is well known, only that oxygen in solution is effective for fermentation. Oxygen is preferably introduced in the form of fine bubbles through a suitable device such as a sparger represented by the reference numeral 38. The actual dissolved oxygen content is determined by dissolved oxygen probe 26. Rate of mass transfer of oxygen from the gas phase to the liquid phase is a function of the agitation speed and the airfeed rate. Controller 27 receives information from probe 26 and compares this information with a set point corresponding to the optimum dissolved oxygen concentration. As is well known, if the dissolved oxygen concentration becomes low enough to interfere with the rate of biosynthesis, either the motor 4 is speeded up, or the rate of introduction of air through line 13 is increased by opening controllable valve 28. In general, it is preferable to increase the speed of motor 4 since the increase in mass transfer is a much higher-powered function of the speed of motor 4 than the rate of introduction of air through line 13. However, if the rate of introduction of air is limiting the concentration of dissolved oxygen, then the size of the opening in valve 28 must be increased.

Gas exits from tank 1 through line 29. Generally, biosynthesis processes are carried out at 1.2 atmospheres pressure and valve 31 is designed to hold this pressure. Similarly, the exemplified processes are generally carried out at 30° C and means (not shown) are provided for controlling the flow of cooling water through the jacket (not shown) on said vessel for maintaining said vessel at the selected temperature.

Exit gas line 29 is fitted with sensors as listed in Table I.

TABLE I

| | |
|---|---|
| $Q_2$ | Exit air flow rate |
| $T_2$ | Exit air temperature |
| $P_2$ | Exit air pressure |
| $PO_2$ | Partial pressure of $O_2$ |
| $PCO_2$ | Partial pressure of $CO_2$ |
| EtOH | Partial pressure of ethyl alcohol |

The information supplied by sensors $Q_1$, $T_1$ and $P_1$ can be expressed as liters of air under standard conditions. Knowing the partial pressure of oxygen in air, the rate of oxygen input to tank 1 is then known.

The information supplied by $Q_2$, $T_2$, $P_2$, $PO_2$ and $PCO_2$ again gives the air flow rate which can be expressed in liters per minute at standard conditions but this time in exit line 29. The air flow rate and the partial pressure of oxygen in the exit gas being known, the quantity of oxygen leaving the system becomes known. Subtracting the exit oxygen rate from input oxygen rate gives the oxygen consumption rate as indicated in the box labelled with reference numeral 32. These calculations, of course, are all carried out by electronic means 14.

Similarly, combining the partial pressure of $CO_2$ in the effluent gas with the effluent flow rate gives the rate of $CO_2$ evolution in the fermentation system as shown in box 33.

Dividing the determined $CO_2$ evolution rate by the $O_2$ consumption rate, both being expressed in moles, give the respiratory quotient, termed RQ, which can also be written as $dCO_2/dO_2$. It is the respiratory quotient, calculated by electronic means 14, which is the critical variable on the basis of which control of the direction of the biosynthesis process in tank 1 is achieved. Where, as is the case with yeast cultures, maximum output of cell mass is the objective, it is known that RQ should be about 1.0. Controller 34 is conveniently set to hold RQ between about 0.9 and 1.1. Controller 34 is connected to the feed mechanisms which are the means by which the taking of nutrient from feed tanks 16 and 17 is controlled. As shown in FIG. 1 diagrammatically, controller 34 starts one of pumps 23 and 24 and turns the other off. Specifically, when RQ rises above the preset value, pump 24 is started and pump 23 is stopped. When RQ falls below the set-point value, the converse action is taken. Generally, nitrogen is supplied as ammonium phosphate, at least in part, so that phosphorus, also necessary as a nutrient, is supplied in the proper proportion.

To maximize the yeast formation rate, the average rate at which carbon-containing nutrient feed is supplied must also be controlled. Previously, attempts to optimize the feed rate have been based on off-line analysis of samples taken from the tank or by monitoring the optical density of the tank contents. However, such off-line techniques are inadequate for achieving best results. Here again, it has been found that a calculated quantity can be correlated with the rate of formation of biomass so that on-line real-time control of the culture is available. The calculated quantity is the time derivative of the oxygen consumption rate, namely $d^2O_2/dt^2$. Experiment has shown that when this derivative is greater than zero, the feed rate of carbon source should be increased, and conversely, when the rate of change is less than zero, the feed rate should be decreased.

To provide control of the carbon feed rate, the time derivative of $dO_2/dt$ is calculated by electronic means 14 and the information supplied to controller 36. Controller 36 then adjusts variable valve 20 to control the feed rate from tank 16. Obviously, the same purpose could be achieved by controlling the pumping rate of pump 23. A further method would be to increase the delivery rate from tank 18 containing both carbon and nitrogen sources.

When culture vessel 1 is operated for the purpose of producing alcohol as well as cell mass, the alcohol monitor EtOH is used to follow the progress of the reaction. However, it is not used for control of the system when RQ and $d^2O_2/dt^2$ are used for this purpose; the entire system can also be operated through use of the information provided by this monitor. Monitors and auxiliary devices based either on paramagnetism infra-red or gas chromatrography in combination with appropriate calculation and display accessories are commercially available and are sufficiently well developed to serve for complete control of the metabolic activity and direction of the system.

To follow the progress of the reaction it is necessary to use the data from the alcohol monitor which yields, by the use of an infra-red sensor, the concentration of alcohol in the effluent stream. Also, the vapor pressure of alcohol is known as a function of alcohol concentration in the culture at the temperature of operation, this usually being 30° C. Consequently, the concentration of alcohol in the culture can be calculated from the concentration of alcohol in the effluent stream by means of the readily measurable functional relationship correlating the two quantities. Such functional relationships may be stored in a memory indicated by the reference numeral 37 in the electronic calculator 14. This memory 37 may also include constants such as the percentage of oxygen in the air, Henry's law constant for alcohol in water and the molecular weights of $O_2$ and $CO_2$, memory 37 also serving to supply such weights when controlling the process metabolism by way of RQ and the time derivative of $dO_2/dt$.

Tank 16 is labelled to indicate that it is a source of carbon and tank 17 is labelled to indicate that it is a source of nitrogen. However, switching back and forth between carbon and nitrogen feed is similar to an on-off system so that control is relatively rough. An alternate method, once a desired C/N ratio has been selected, is to fill tank 16 with a mixture of nutrients in which the ratio of carbon to nitrogen is somewhat higher than the desired ratio, and to fill tank 17 with a mixture in which the ratio of carbon to nitrogen is somewhat lower than the desired ratio. Consequently, when controller 34 cuts feed off from one tank and turns on the other, the intensity of the pulse engendered by the change is much smaller, and control is therefore much smoother. For instance, where a C/N of 2:1 is desired as in batch operation, the C/N ratio in tank 16 could be between 3 and 5 and in tank 17 could be between 3 and 5 and in tank 17 could be between 0 and 1. A ratio of 0, of course, corresponds to absence of any carbohydrate nutrient from tank 17.

While a C/N ratio of about 2.0 is desirable for maximization of production of cell mass, especially is batch operation, satisfactory results can be obtained at C/N values between 2 and 7. Where high alcohol production is desired, the ratio should be held between about 15 and 22, with a value between about 17.5 and 18.5 being best. It should also be noted that although alcohol cannot be produced without simultaneous biosynthesis of cell mass, cell mass cannot be produced without simultaneous production of some ethyl alcohol. Nevertheless, when C/N is at 2.0, and, in general, not greater than 7, the production of ethyl alcohol is economically negligible.

Based on the composition of cell mass, C/N should theoretically be close to 5.0. For continuous operation of a fermentor, a feed ratio in the range of 4 – 6 gives an excellent rate of production of cell mass, termed dDw/dt in FIG. 2.

Where the optimum C/N is known it is possible to feed from a single tank such as tank 18 containing the nutrients in the desired ratio. The only variable which must then be controlled is the rate of feed. This task, again, is carried out by controller 36 which can control the rate of feed from tank 18 either by controlling the operation of pump 25 of adjustable valve 22 on the basis of $d^2O_2/dt^2$.

Figure 2:
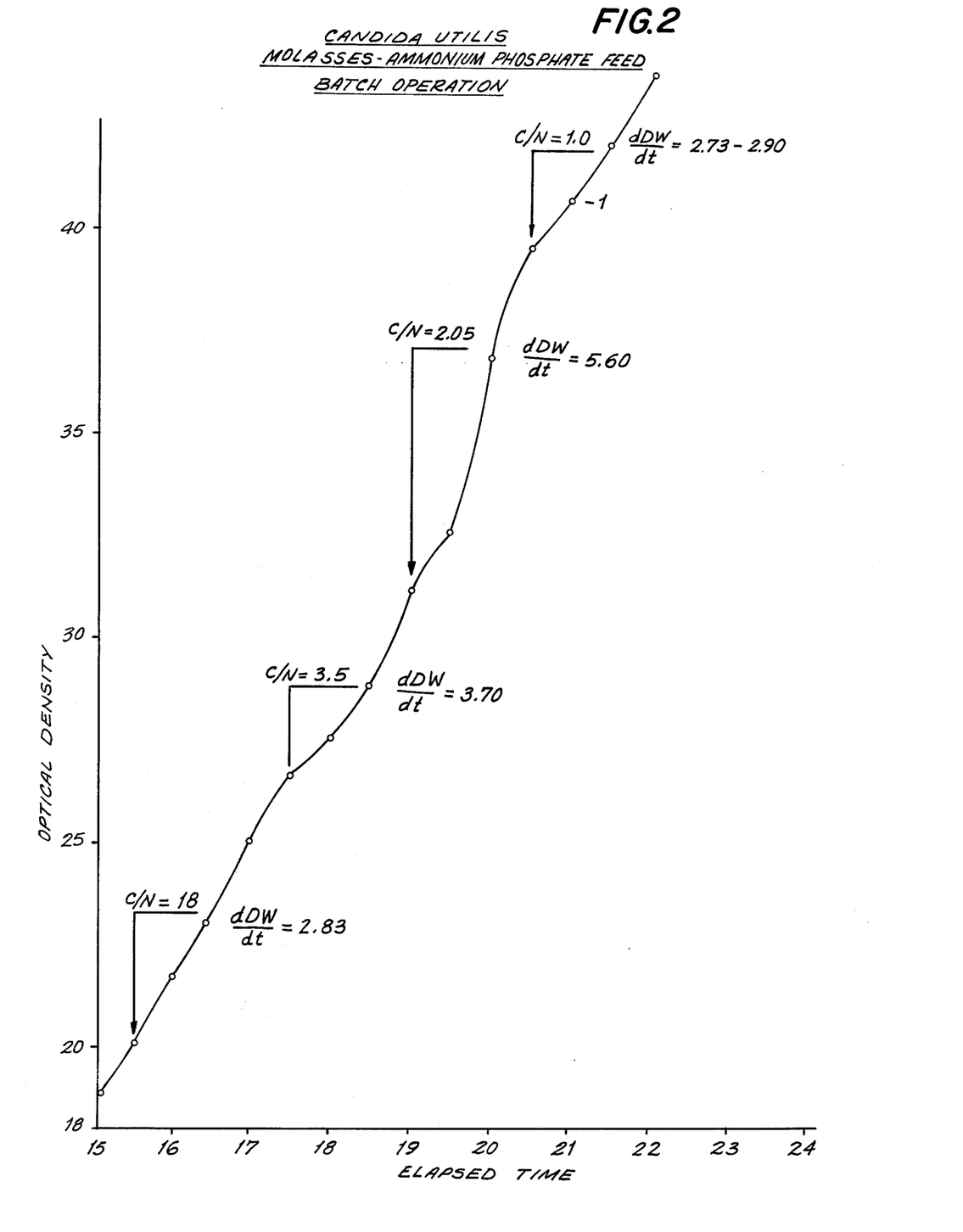
FIG. 2 shows how arbitrary changes in the ratio of carbon to nitrogen in the feed changes the rate of cell growth.

The effect of C/N on the rate of production of cell mass in batch operation is shown in FIG. 2. The concentration of cell mass is determined from a known functional relationship between the optical density of the tank contents and the concentration of cell mass. The ordinate in FIG. 2 is Optical Density. The span of time over which C/N is maintained at any given value is indicated by the horizontal line under the listed values in the Figure. The rate of increase of cell mass is specified to the right of the curve for each value of C/N. As can be seen, for the four values tested the rate of production was maximized when C/N was 2.05, namely, close to 2.0. Also, when C/N was set at 18, the rate of production of cell mass was 2.83 grams per liter per hour, and, although not shown in the Figure, the rate of production of alcohol was maximized at this value of the ratio.

Figure 3:
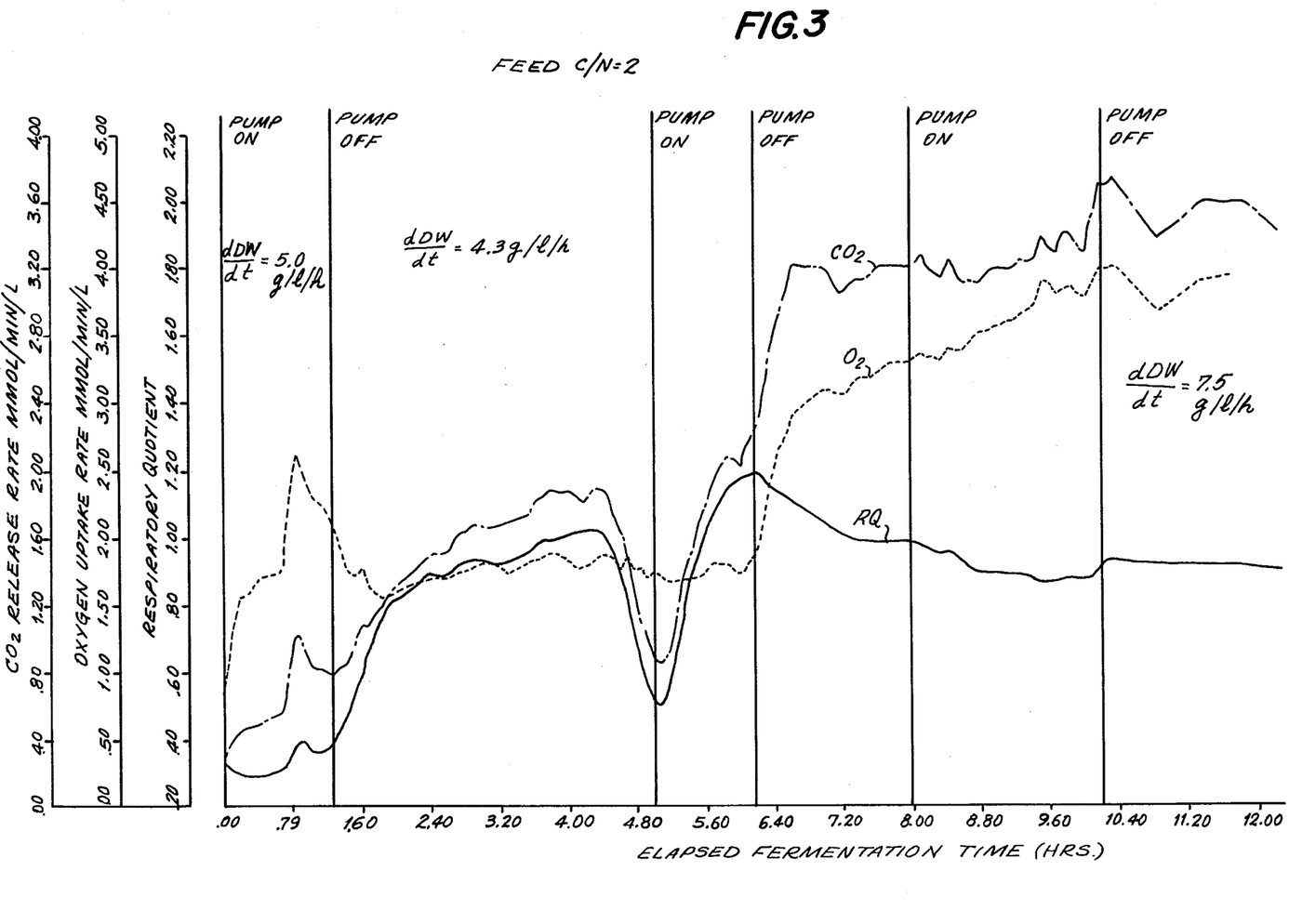
FIG. 3 shows how the rates of $CO_2$ evolution, $O_2$ consumption and respiratory quotient are affected by the operation a feed pump in on-off mode.

The type of control achieved with feed from a single tank at a fixed C/N ratio with the pump supplying the feed being operated in the on-off mode is shown in FIG. 3. FIG. 3 includes three curves, these showing the rate of $CO_2$ evolution, the rate of $O_2$ uptake and the respiratory quotient. Stability of the system was initially relatively poor, although rates of cell mass growth were high compared to conventional yields. However, after about 8 hours of operation, the rates of evolution of $CO_2$ and $O_2$ uptake became fairly constant as did the respiratory quotient at a value close to 1.0. Also, the rate of cell mass production rose to 7.5 g/L/hour. The value of $dO_2/dt$ also confirmed this observation. Control by the use of alternating feed from tanks 16 and 17 when tank 16, at least, contains a mixture of nutrients rather than a single carbon source, is much closer.

The type of control described has been applied to the family of organisms termed Cryptococcaceae. The principal genus within this family which is suitable is Saccharomyces. The species which have been found most useful are Saccharomyces cerevisiae, Candida utilis, Candida guillermondii and Candida tropicalis. Examples of the use of such organisms follow.

EXAMPLE 1

A culture medium with a volume of 150 liters was prepared by dissolving the following components:
6,000 g. sucrose
100 g. peptone
20 g. $K_2HPO_4$ and 20 g. $KH_2PO_4$
100 g. corn-steep liquor
100 g. $MgCl_2$
1,200 g. $(NH_4)_2HPO_4$
10 g. silicone MSA antifoaming agent The pH was adjusted to 6.5 using 4N KOH and 4N $H_3PO_4$. After sterilization, the culture medium temperature was set to 30° C, the agitation speed to 200 RPM, the sterile are sparge rate to 150 SLPM, which amounts to 1.0 VVM based on the volume of culture medium, and the vessel head pressure to 1.2 atm. The temperature, pressure, agitation speed and air feed rate were maintained constant throughout the process.

To tank 16 was added a sucrose solution containing 50 g of sucrose per liter. The tank and its contents were then sterilized. To tank 17 was added a 30% ammonium hydroxide solution. The RQ set point on the controller was set to maintain at about 1.0, actually between 0.9 and 1.1. The culture was inoculated with Candida utilis strain ATCC 9226 at a concentration of 12 g cell mass per liter (dry weight).

In the early exponential phase of growth, the RQ value started to increase above 1.1. Controller 34 actuated pump 24 to deliver ammonium hydroxide solution from tank 17 at a rate of 0.0175 L/hr. As a result, RQ began to drop. When it dropped below 1.0, pump 23 was actuated to deliver sucrose solution at a rate of 1 liter/hr. Delivery of sucrose solution continued unitl RQ rose above 1.0 at which point pump 23 shut down and pump 24 was activated again. The process was continued until biosynthesis was terminated. Integration of the quantities of sucrose solution and ammonium hydroxide delivered showed that the time-average for C/N was close to 2 during the exponential growth phase and near 5 for the remainder of the fermentation period.

During the biosynthesis, the pH of the culture was maintained at 6.5 ± 0.1 by the addition of 4N $H_3PO_4$.

The ethyl alcohol concentrations in the culture liquid and in the exit gas were measured by the method of Kozelka and Hine and by an automatically recording infra-red ethyl alcohol analyzer, respectively. The rate of ethyl alcohol formation was found to be 0.1 g/L/hr, while the cell-mass formation rate was found to be 4.5 g/L/hr (on a dry weight basis).

The fermentation was terminated at 5.5 hours and was examined for cell-mass and carbohydrate content. The total cell mass was 39.31 g/L (dry weight, 8% moisture) with virtually no reducing sugar present. Consequently, the yield was $Y = 0.60$ as weight of dry cell-mass per weight of carbohydrate supplied to the culture.

The cells from the slurry were removed by means of filtration and were further processed to obtain single cell protein for feed or food supplementation, this being a principal use for cell mass produced in this way.

EXAMPLE 2

A culture medium was prepared by mixing and dissolving the following components:

100 g. peptone
20 g. $K_2HPO_4$
20 g. $KH_2PO_4$
100 g. corn-steep liquor
100 g. $MgCl_2$
2,820 g. $(NH_4)_2HPO_4$
10 g. silicone MSA antifoaming agent
150 liters of cellulose hydrolysate containing
50 g. glucose as fermentable sugar per liter.

The pH was adjusted to 5.0 with 4N KOH and 4H $H_3PO_4$.

After sterilization the culture medium temperature was set to 30° C, the agitation speed to 100 RPM, sterile air sparge rate to 150 SLPM (10 VVM) and the vessel head pressure to 1.2 atm. The temperature, the pressure and the liquid pH were maintained constant during the process whereas the agitation speed and air flow rate varied from 100 to 500 RPM and 100 to 200 SLPM, respectively, in order to maintain the dissolved oxygen concentration set point requirement at 25% of the dissolved oxygen saturation value, this control being exercised by controller 27.

Cellulose hydrolysate containing 100 g of glucose/liter was sterilized in tank 16. A 50% solution of $(NH_4)_2HPO_4$ was prepared and sterilized in tank 17. A mixture of cellulose hydrolysate with $(NH_4)_2HPO_4$ from the separately sterilized components was placed in tank 18. The C/N ratio in this tank was 5:1, the concentration of the glucose and $(NH_4)_2HPO_4$ being respectively 100 g/L and 37.6 g/L.

Growth was started with the inoculation of the culture medium with Candida utilis ATCC 9226 (NCTC) at a concentration of 12 g cell-mass/L (dry weight). The RQ set point on the controller was set at about 1.0, namely between 0.9 and 1.1.

In the early exponential phase of growth, RQ began to increase above 1.1. The controller actuated pump 24 to deliver $(NH_4)_2HPO_4$ solution from tank 17 at a rate of 1.10 liters per hour. As a result, the respiratory quotient started to fall below 1.0, which, in turn actuated pump 16 to deliver glucose containing cellulose hydrolysate from tank 16 at a rate of 15.0 L/hr. RQ rose until it exceeded 1.1 at which point pump 24 was activated. A time average of delivered feed showed that the C/N ratio was 5:1. During this part of the fermentation the pH of the culture was controlled at 5.0 ± 0.1 by the addition of 4N HCl.

Ethyl alcohol was formed at a rate of 0.05 g/l/hr and cell-mass formation rate proved to be 6.2 g/l/hr.

After 5 hours of fermentation, 50% of the fermentation broth (81.10 l) was removed. Analysis of the slurry showed a cell-mass content on a dry basis of 64.8 grams per liter and no fermentable sugar.

The slurry removed was replaced by addition of 81.10 liters of the mixture from tank 18, bringing the fermentable sugar content of the slurry in tank 1 to 54.07 g/L and the C/N ratio to about 5.

The respiratory quotient started to increase to 3.0. The RQ controller was disconnected so that no corrective action based on the RQ set point was performed electronically. This resulted in an increase in ethyl alcohol formation to a rate of 1.8 g/L/hr and the growth rate of cell mass dropped to 1.2 g/L/hr on a dry weight basis.

The RQ controller was actuated once more. Pump 17 was first put into operation by the RQ controller, delivering $(NH_4)_2HPO_4$ at a rate of 1.10 L/hr. RQ dropped continuously to 0.9 at which point the ethyl alcohol formation rate was found to thave dropped to 0.07 g/L/hr and the cell-mass production rate was found to have increased to 4.3 g/L/hr.

The removal of 50% of the contents of tank and replacement with fresh nutrient mixture from tank 18 was repeated twice more over the course of the next 11 hours. As a result, in a total of 16 hours fermentation time, 324.4 liters of culture liquid were processed resulting in a production of 19,334 grams of dry cell-mass which is equivalent to 59.6 grams per liter. The yield based on the carbon supplied was 0.6.

It will be noted that this mode of operation is not restricted to removal of any particular fraction of the contents of tank 1. Thus, it would be possible to remove 20% of the tank contents, say, at intervals of 90 minutes, each, with subsequent refilling of the tank with fresh nutrient. This type of operation may well be termed semi-continuous.

The cells from the slurry obtained in this example were separated off by filtration and further processed to obtain single cell protein for feed and food supplement.

EXAMPLE 3

Fermentor tank 1 was fitted with overflow pipe 39 and valve 41 in said overflow pipe. The top of the overflow pipe 39 was placed so that continuous removal of slurry would result when the liquid level was raised above the corresponding to 160 liters of culture in the tank.

A culture medium having a volume of 150 liters was prepared containing:

100 g. peptone
20 g. $K_2HPO_4$
20 g. $KH_2PO_4$
100 g. corn-steep liquor
100 g. $MgCl_2$
11.5 l. unsulphured molasses cntaining 60% of fermentable reducing sugar,
750 g. $(NH_4)_2HPO_4$
10 g. silicone MSA antifoaming agent.

The pH of the culture was adjusted to 5.5 with 4N KOH and/or 4N $H_3PO_4$. After pasteurization, the following process variables were established:

Temperature 30° C, head-pressure 1.2 atm, agitation speed 200 RPM, sterile air flow rate 160 SLPM. The process variables were maintained at these values throughout the process. Tank 16 was filled with unsulphured a nutrient complex diluted 1:1 with tap water and addition vessel 17 was filled with a 30% solution of ammonium sulphate. Addition vessel 18 was filled with molasses containing 56 g $(NH_4)_2SO_4$ and molasses of 60° Briix in dissolved form. The C/N value for this solution was 20.

The culture was inoculated with *Saccharomyces cerevisiae var. elipsoideus* (ATCC 560) (50 million cells per ml). After four hours of fermentation RQ rose to 4.0 and the formation of ethyl alcohol started. At this point the RQ controller was actuated with a set point near 4.0, actually 3.8 – 4.2. Also the feed tank 18 was started at a rate of 16 l/hr.

The rate of ethyl alcohol formation varied between 3.0 and 4.8 g/l/hr and the value of RQ showed a tendency to increase above 4.2. The RQ controller then brought pump 24 into action with a frequency such that the feed from tank 17 was in excess of 0.15 l/hr.

As aforenoted, the rate of ethyl alcohol formation varied between 3.0 and 4.8 g/l/hr. During this same period, the cell growth rate was found to vary between 1.0 and 1.75 g/l/hr.

During the continuous operation, the slurry, in addition to separating off the cell mass, was further processed by conventional distillation to obtain 36% ethyl alcohol, and the residue from the distillation was discarded.

EXAMPLE 4

A culture medium having a volume of 150 liters was prepared containing:
3,000 g. sucrose
100 g. peptone
20 g. $K_2HPO_4$ and 20 g. $KH_2PO_4$
100 g. corn-steep liquor
100 g. $MgCl_2$
1,200 g. $(NH_4)_2HPO_4$
10 g. silicone MSA antifoaming agent The pH was adjusted to 6.5 using 4N KOH and 4N $H_3PO_4$. After sterilization, the cluture medium temperature was set to 30° C, the agitation speed to 200 RPM, the sterile air sparge rate to 150 SLPM, and the vessel head pressure to 1.2 atm. The temperature, pressure, agitation speed and air feed rate were maintained constant throughout the process.

Nutrient tanks 16 and 18 were filled with unsulphured molasses, diluted with tap water 1:1. The reducing sugar content of the molasses was thus 290 g/l. Nutrient tank 17 was filled with 30% $NH_4OH$.

The culture medium was inoculated with *Saccharomyces cerevisiae var. elipsoideus* (ATCC 560) (50 million cells per ml). The starting cell mass concentration was 12 g/l (dry weight).

The molasses feed rate from tank 18 was established in accordance with the derivative of the oxygen uptake rate, namely, $d^2O_2/dt^2$, this value being calculated on the basis of exit $O_2$ gas analysis, off-gas temperature and pressure as well as gas flow rate. The rate of addition of molasses from tank 18 was in accordance with the otherwise known fact that for the complete oxidation of 1 molecule of glucose, 6 molecules of oxygen are required.

The set-point on the RQ controller 34 was 0.9 – 1.1. RQ was held in the desired range by alternate activation of pumps 23 and 24 with their valves 20 and 21, respectively, in order to introduce ammonium hydroxide from tank 17 and molasses from tank 16. When the value of RQ increased, delivery of ammonium hydroxide from tank 17 was started. Conversely, when the value of RQ decreased, molasses was introduced from tank 16. The average rate of delivery of $NH_4OH$ was 5.98 l/hr. The average rate of delivery of molasses from tank 16 was 0.500 l/hr.

Overflow tube 39 served for continuous removal of culture liquid as the volume increased due to the continuous addition of molasses from tank 18 as required by the oxygen uptake of the culture. The average oxygen uptake rate obtained in the exponential phase of growth was 432 mM/L/hr., which is equivalent to a cell growth rate of 7.5 g/L/hr (dry weight). This required the addition of molasses from tank 18 at a rate of 28.5 L/hr. (time average rate).

During this operation the ethyl alcohol concentration measurements in the off-gas and in the solution indicated a formation rate of 0.05 g/L/hr.

Cell mass was obtained from the culture liquid overflowing through tube 39 by means of conventional centrifugation.

As is evident from the preceding examples, it is possible to operate a fermentation process in accordance with the present invention in any of the modes, batchwise, semi-continuously or continuously. Further it is possible to control the nature of the product obtained by establishing the critical ratio C/N at appropriate values or, more precisely, within appropriate ranges of values. Further, a parameter, namely, the respiratory quotient has been found which makes it possible to effect on-line, real-time control of a fermentation process. The process can be controlled to provide an output of selected product or products without either on-line or off-line monitoring of the product or products themselves. This valuable parameter is obtained by essentially continuous monitoring of the $CO_2$ and $O_2$ contents of the off-gases from the fermentor and by essentially continuous calculation of RQ from these data. On the basis of previous experimentation, RQ can be set to a specified value and the feeds of nutrients controlled in the proper ratio and at the proper rates to deliver selected products with optimum yield on the basis of fermentable carbohydrate consumed. Needless to say, the other essential nutrients such as phosphorus, magnesium, sulphur and chloride must also be supplied in adequate amounts, but the proportions are not critical if kept below toxic level.

A second valuable parameter has also been established, this parameter being the time derivative of $d^2O_2/dt^2$. On the basis of this parameter the feed rate of nutrient can be controlled to maximize the rate of biosynthesis.

It will thus be seen that the objects set forth above, among those made apparent from the preceding description, are efficiently attained, and since certain changes may be made in carrying out the above method and in the construction set forth without departing from the spirit and scope of the invention, it is intended that all matter contained in the above description and shown in the accompanying drawings shall be interpreted as ilustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An improvement in the method of operation of a fermentation tank with the objective of producing any desired ratio of weight of ethyl alcohol to weight of cell mass, designated as EA/CM, between a maximum corresponding to the maximum concentration of ethyl alcohol which the cell can tolerate, and essentially zero, said tank being supplied with oxygen, metabolizable carbon, nitrogen and phosphorus, the weights of carbon and nitrogen supplied as compounds thereof being designated as C and N. respectively and the feed ratio of carbon to nitrogen being termed C/N, said fermentation tank being maintained at selected optimum temperature, pressure, pH and dissolved oxygen level, wherein said improvement comprises as a preliminary step:
   a. varying the ratio C/N and noting the value of EA/CM corresponding to each value of C/N, thereby establishing a functional relationship between C/N and EA/CM, and as a control step during actual operation,
   b. holding said feed ratio C/N at a value appropriate for producing said desired EA/CM ratio.

2. The improvement as defined in claim 1 wherein said feed ratio is maintained between about 2 and 7, the objective being to maximize the rate of production of cell mass.

3. The improvement as defined in claim 1, wherein said feed ratio is held between about 15 and 22, the objective being to maximize the rate of production of ethyl alcohol.

4. The improvement as defined in claim 1, wherein said fermentation tank is operated continuously, and said feed ratio is maintained between about 4 and 6, the objective being to maximize the rate of production of cell mass.

5. The improvement as defined in claim 1, wherein said feed ratio is held between 17.5 and 18.5, the objective being to maximize the production of ethyl alcohol.

6. The improvement as defined in claim 1, wherein said fermentation utilizes a culture from the family of Cryptococcaceae.

7. The improvement as defined in claim 1, wherein said fermentation utilizes a culture selected from the group of genera consisting of Oosporum, Saccharomyces and Candida.

8. The improvement as defined in claim 1, wherein said fermentation utilizes Candida utilis.

9. The improvement as defined in claim 1, wherein said nitrogen is supplied in the form of a memeber selected from the group consisting of $NH_3$, $NH_4OH$, $(NH_4)_3PO_4$, $(NH_4)_2SO_4$, organic nitrogen and mixtures thereof.

10. The improvement as defined in claim 9, wherein said member is so selected that the concentrations of sulfate and phosphate ions in said fermentation tank remain below levels such as would inhibit the rate of fermentation in said tank.

11. The improvement as defined in claim 1, further comprising the steps of emptying said fermentation tank, separating the single cells therein as well as any alcohol in economically significant quantity therein from the fermentation mixture, and refilling said tank with fresh culture and nutrients.

12. The improvement as defined in claim 1, further comprising the steps of removing a fraction of the contents of said fermentation tank, separating single cell mass as well as any alcohol in economically significant quantity therein from said fraction and refilling said tank with fresh nutrient.

13. The improvement as defined in claim 1, further comprising the steps of removing the contents of said tank in an essentially continuous stream, separating the single cell mass as well as any economically significant quantity of alcohol therein from said stream and supplying fresh substrate to said tank at a volumetric rate essentially equivalent to the rate of removal of said stream.

14. The improvement as defined in claim 13, wherein the rate of removal of slurry is such that the rate of conversion of substrate to desired end product is approximately maximum.

15. The improvement in the method as defined in claim 1, wherein said fermentation tank is operated batchwise and said feed ratio C/N is maintained at about 2, the objective being to maximize the production of cell mass.

16. An improvement in the method of operation of a fermentation tank with the objective of producing any desired ratio of weight of ethyl alcohol to weight of cell mass, said ratio being designated as EA/CM, between a maximum corresponding to the maximum concentration of ethyl alcohol which the cell can tolerate, and essentially zero, said tank being supplied with oxygen, metabolizable cabon, nitrogen and phosphorus, the weights of carbon and nitrogen being designated as C and N. respectively, the ratio of feed rates of C and N being designated C/N, said fermentation tank being maintained at selected optimum temperature, pressure, pH and dissolved oxygen level, wherein said improvement comprises as preliminary steps:
   a. feeding oxygen to said fermentation tank at a known feed rate and measuring the output rate of oxygen and carbon dioxide from the tank so that the rates of $CO_2$ evolution, namely $dCO_2/dt$ and $O_2$ uptake, namely $dO_2/dt$ in mols are known, t indicating time;
   b. calculating the ratio of the rate of $CO_2$ evolution to the rate of $O_2$ uptake, said ratio being designated as RQ;
   c. sampling the contents of said tank and measuring the cell mass content thereof and measuring the alcohol vapor leaving said tank and calculating EA/CM from said measurements;
   varying C/N over a selected range and calculating both RQ and EA/CM as C/N is varied, thereby estalishing functional relationships between RQ and C/N, RQ and EA/CM, and C/N and EA/CM, so that a desired EA/CM can be correlated with a specific value of RQ and
   d. determining the functional relationship between RQ and the ratio of ethyl alcohol to cell mass produced to establish the optimum RQ for a desired EA/CM.
   e. as operating steps, measuring $dO_2/dt$ and $dCO_2/dt$ and calculating RQ, all automatically on a real time, on-line basis; and
   f. when RQ deviates from the value corresponding to said desired EA/CM increasing C/N when RQ drops below said value and vice versa 17. The improvement as defined in claim 16, further comprising the steps:
   g. calculating $d^2O_2/dt^2$ the first derivative of the rate of oxygen consumption by said cell mass; and h. increasing the feed rate of at least metabolizable carbon when $d^2O_2/dt^2$ is positive and decreasing the feed rate of at least metabolizable carbon when $d^2O_2/dt^2$ is negative, whereby the feed rate of metabolizable carbon is adjusted to the maximum rate at which the cell can consume carbon.

18. The improvement as defined in claim 17, wherein at lest steps (g) and (h) are carried out automatically on an on-line, real-time basis.

19. An improvement in the method of operation of a fermentation tank with the objective of producing any desired ratio of weight of ethyl alcohol to weight of cell mass, designated as EA/CM, between a maximum corresponding to the maximum concentration of ethyl alcohol which the cell can tolerate, and essentially zero, said tank being supplied with oxygen, metabolizable carbon, nitrogen and phosphorus, the weights of carbon and nitrogen supplied as compounds thereof being designated as C and N respectively and the feed ratio of carbon to nitrogen being termed C/N, said fermentation tank being maintained at selected optimum temperature, pressure, pH and dissolved oxygen level the functional relationships between C/N and RQ, C/N and EA/CM and RQ and EA/CM having been determined, where RQ is the ratio in mols of the rate of $CO_2$ evolution namely $dCO_2/dt$, to the rate of $O_2$ uptake namely $dO_2/dt$ being time and said ratio being $dCO_2/dO_2$ wherein said improvement comprises.

a. measuring the rates of $CO_2$ evolution, and $O_2$ uptake, in mols in said tank, b. calculating RQ on an on-line real-time basis, and, c. adjusting C/N to hold RQ at a selected value C/N being increased when RQ falls below said value and vice versa.

* * * * *